United States Patent [19]

Roth

[11] Patent Number: 4,911,164
[45] Date of Patent: Mar. 27, 1990

[54] SURGICAL TOOL AND METHOD OF USE

[76] Inventor: Robert A. Roth, 29 Hyslop Rd., Brookline, Mass. 02146

[21] Appl. No.: 186,174

[22] Filed: Apr. 26, 1988

[51] Int. Cl.[4] ............................................. A61B 17/04
[52] U.S. Cl. ..................................................... 606/148
[58] Field of Search .................. 128/343, 345, 334 R, 128/311, 339, 340, 303 R, 898; 604/105–107, 272; 112/12–14, 63

[56] References Cited

U.S. PATENT DOCUMENTS

| | | | |
|---|---|---|---|
| 2,072,346 | 3/1937 | Smith | 604/105 |
| 2,897,820 | 8/1959 | Tauber | 128/334 R |
| 4,553,543 | 11/1985 | Amarasinghe | 128/334 R |
| 4,784,139 | 11/1988 | Demos | 128/339 |

Primary Examiner—Michael H. Thaler
Assistant Examiner—William Lewis
Attorney, Agent, or Firm—Lackenbach Siegel Marzullo & Aronson

[57] ABSTRACT

A surgical suture guide, has an elongated body with a substantially straight portion and an end portion with a rounded tip at one end of the elongated body. A curved portion is situated between the substantially straight portion and the end portion. A guide arrangement having at least one groove extends from the tip into the end portion.

28 Claims, 4 Drawing Sheets

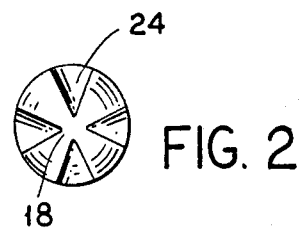
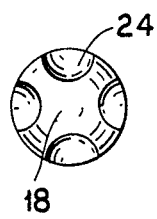
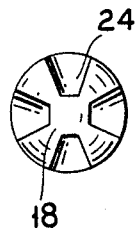
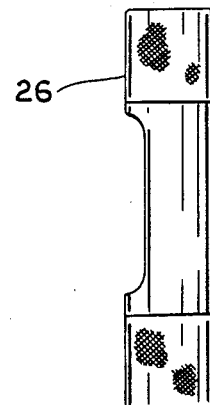
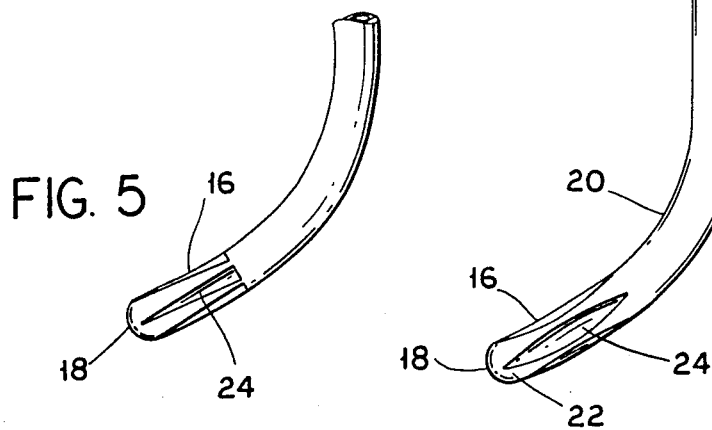

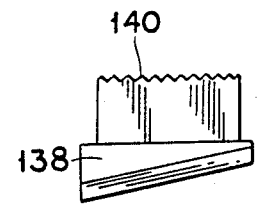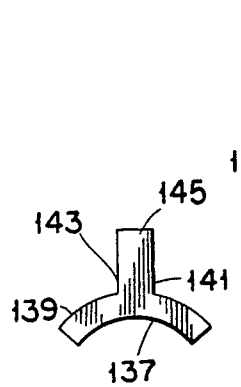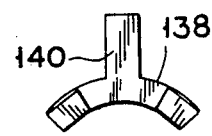
FIG. 9A   FIG. 9B   FIG 9C
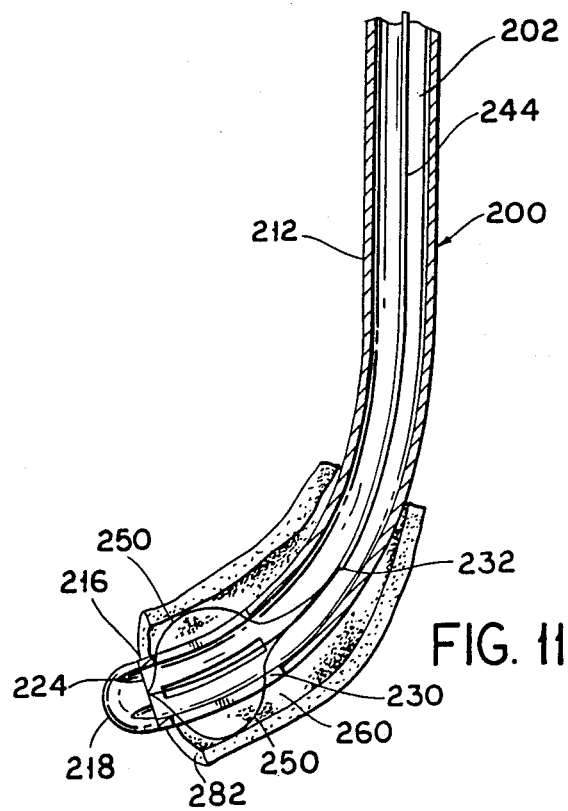
FIG. 11

SURGICAL TOOL AND METHOD OF USE

BACKGROUND OF THE INVENTION

This invention relates to a medical device and method for placing surgical sutures.

In particular this invention relates to a surgical suture guide and a method for placing sutures through a cut portion of a body of an animal including a human when this portion has a tubular configuration.

In one embodiment, this invention relates to a surgical suture guide for and method of placing urethral sutures through a cut portion of a urethral meatus when the urethral meatus is surrounded by an adjacent tissue.

Radical retropubic prostatectomy is established as an effective method for the treatment of patients with localized carcinoma of the prostate gland. In the past, certain intraoperative and postoperative complications led some surgeons to favor other forms of treatment. Walsh in the publication "Radical Retropubic Prostatectomy"; Walsh PC, Gittes RF, Perlmutter AD, Stamey TA (eds); *Campbell's Urology*, 5th ed, Philadelphia, W B Saunders, 1986, pp 2754–2775 (which the present application incorporates by reference) provides detailed descriptions of the neurovascular anatomy of the apex of the prostate and describes an operative technique. It has been reported that based on this publication surgeons were able to reduce the incidence of complications, such as intraoperative hemorrhage, postoperative erectile impotence, and stricture formation. Walsh's technique permits the surgeon to control bleeding from the prostatic dorsal venous plexus reliably and thus to improve visualization of the apex of the prostate for controlled dissection and subsequent urethrovesical anastomosis.

However, some technical problems still remain. After division of the urethra at the apex of the prostate and removal of the prostate, the stump of the urethra retracts into the adjacent tissue, the urogenital diaphragm. Reexposure of the urethra has remained an important and frustrating task. Various solutions have been suggested. A first technique is to place sutures directly alongside a Foley catheter, which acts as a guide in identifying the lumen of the urethra. Placement of these sutures can be difficult and imprecise, and often the muscle of the urogenital diaphragm and the wall of the catheter are caught in the suture. As an added inconvenience, these sutures are usually placed inside to outside, and the needle requires rearming to complete the urethrovesical anastomosis. A second technique is to place several sutures into the cut edge of the urethra before complete division. After complete division, traction is applied to these sutures, exposing the stump away from adjacent tissue for additional suture placement. However, tension on these sutures can inadvertently lacerate the urethral stump and make further suture placement even more difficult. A third technique has been to position the patient's legs in stirrups and apply direct pressure to the perineum to push out the adjacent tissue, the urogenital diaphragm, and the urethra for direct suture placement. Another solution involves the placement of vesicoperineal pulldown sutures along with Foley catheter drainage. If all of these techniques fail, a Foley catheter can be placed into the bladder and the bladder pulled down onto the urogenital diaphragm with the hope of obtaining healing by secondary intention. These techniques are proved to be time-consuming and unreliable.

SUMMARY OF THE INVENTION

This invention comprises a surgical suture guide, with an elongated body having a substantially straight portion, an end portion with a rounded tip at one end of the elongated body, a curved portion situated between said substantially straight portion and said end portion, guide means having at least one groove extending from said tip into said end portion. In various embodiments the groove has a substantially triangular cross-section, an arc shaped cross-section, or a trapezoidal shaped cross-section. In some embodiments the groove extends into said curved portion of the elongated body, or from a center of the rounded tip into the end portion and the curved portion. In particular embodiments a handle is provided at an end of the substantially straight portion. In additional embodiments a projection of the groove on an outside surface of the elongated body defines an elongated ellipse, or a cone. In a particular application the cone faces the rounded tip and in further embodiment the elongated body has a substantially circular cross-section.

This invention also includes a method of placing urethral sutures through a cut portion of a urethral meatus wherein the urethral meatus is surrounded by adjacent tissue by means of a suture guide; wherein the suture guide comprises an elongated body having a substantially straight portion, and end portion with a rounded tip at one end of the elongated body, a curved portion situated between said substantially straight portion and said end portion, guide means having at least one groove extending form said tip into said curved portion;

wherein the method comprises of the following steps;

(a) inserting the suture guide into and through the urethral meatus in such a way that at least the rounded tip and a part of the groove protrude from the cut urethral meatus pushing said cut urethral meatus out of the adjacent tissue;

(b) inserting a suturing device into said protruding groove; and (c) supporting and guiding said suturing device along the groove while placing a suture in the urethral meatus.

In one embodiment the method further comprises the steps of (d) manipulating the substantially straight portion to expose another site of the cut urethral meatus for placing the sutures; and (e) repeating the steps "b", "c" and "d".

In some embodiments step "d" further includes rotating of said substantially straight portion and moving the groove around an internal surface of the cut urethral meatus and exposing an additional site for suture placement.

In some embodiments of the method a handle is provided at an end of the substantially straight portion.

Furthermore, in some embodiments of the method in step "b" the suturing device is inserted between an inside surface of the urethral stump and said groove.

In various embodiments of the method the groove has a substantially triangular cross-section, an arc shaped cross-section, or a substantially trapezoidal shaped cross-section.

In particular embodiments of the method a projection of said groove on an outside surface of the elongated body defines an elongated ellipse or a cone.

Another embodiment of the invention is a method of placing surgical sutures through a cut portion of a body of an animal including a human having a tubular configuration wherein said tubular portion is surrounded by adjacent tissue by means of a suturing guide, said suturing guide comprising an elongated body having a substantially straight portion, an end portion with a rounded tip at one end of the elongated body, a curved portion situated between said substantially straight portion and said end portion, guide means have at least one groove extending from said tip into said curved portion; wherein the method comprises of the following steps:

(a) inserting said suture guide into and through the cut tubular part in such a way that at least said rounded tip and a part of said groove protrude from said cut portion of the body pushing said cut portion of the body out of the adjacent tissue;

(b) inserting a suturing device into said protruding groove; and (c) supporting and guiding said suturing device along the groove while placing a suture in the part of the body having tubular configuration, which may further include (d) manipulating said substantially straight portion to expose another site of the tubular part for placing the sutures; and (e) repeating the steps of "b", "c" and "d", wherein the step "d" further includes rotating of said substantially straight portion and moving said groove around an internal surface of the tubular part and exposing an additional site for suture placement.

In one embodiment of such method a handle is provided at an end of the substantially straight portion.

In a particular method is wherein in the step "b" the suturing device is inserted between the interior of the tubular part and said groove.

In some embodiments of the method the groove has a substantially triangular cross-section, an arc shaped cross-section, of a substantially trapezoidal shaped cross-section.

In various embodiments of the method a projection of the groove on an outside surface of the elongated body defines an elongated ellipse, or a cone.

The invention also includes a surgical tool comprising an elongated body made of a substantially hollow tubular structure, said elongated body having a substantially straight portion, an end portion and a rounded tip at one end of the elongated body, a curved portion situated between said substantially straight portion and said end portion, at least two openings going through a wall of said substantially hollow tubular structure, said openings extending from said rounded tip to at least said end portion, guide means having at least one groove for guiding a suturing device, and expanding means having at least two expanding members positioned within the hollow tubular structure, each said expanding member having an contacting portion to be guided by said openings, activating means at least partially situated within said hollow tubular structure for activating said expending members in a such manner that at least a contacting portion of each said expanding member passes through said opening and protrudes beyond an outside surface of the elongated body.

The invention further comprises the tool wherein said guide means is at least one groove positioned within the wall of the substantially hollow tubular structure between said openings, said groove extends from said rounded tip into at least said end portion, or wherein said groove is positioned within said contacting portion.

In some embodiments each said expanding member has a base portion with upper and lower surfaces and the contacting portion which is connected to the upper surface of the base portion, which may include an activating means comprising a frusto-conical member, the lower surface of the base portion is adapted to closely receive an outside surface of the frusto-conical member, whereby, when said frusto-conical member is inserted between said contacting members an outside surface of the frusto-conical member contacts the lower surfaces of the base portion of each said expanding members pressing said contacting portions to protrude beyond the outside surface of the elongated body.

In some embodiments the invention include a surgical tool wherein said expanding members are spaced apart, outwardly bowed spring arms jointed at and attached to an inside surface of said rounded tip, said spring arms are also joined at a place of junction between said activating means and said expanding members, said spring arms are adapted to move form a first-contracting position to a second-expanding position, during said first position said spring arms are situated within the hollow tubular structure and during said second portion said activating means presses said spring arms causing them to expand and to protrude through said openings beyond the outside surface of the elongated body.

BRIEF DESCRIPTION OF THE DRAWINGS

Other advantages and features of the invention are described with reference to preferred embodiments which are intended to illustrate and not to limit the invention and in which:

FIG. 1 is a view of a surgical suture guide.

FIG. 2 is a front view of an end portion of one embodiment of the surgical suture guide.

FIG. 3 is a front view of an end portion of another embodiment of the surgical suture guide.

FIG. 4 is a front view of an end portion of a further embodiment of the surgical suture guide.

FIG. 5 is a view of an end portion of the surgical suture guide.

FIG. 9A is a side view of an expanding member shown in FIG. 6.

FIG. 9B is a front elevational view of an expanding member shown FIG. 6.

FIG. 9C is another side elevational view of an expanding member shown in FIG. 6.

FIG. 11 is a partial cross-sectional view of another embodiment of the surgical tool.

DETAILED DESCRIPTION OF THE INVENTION

Figure 6:
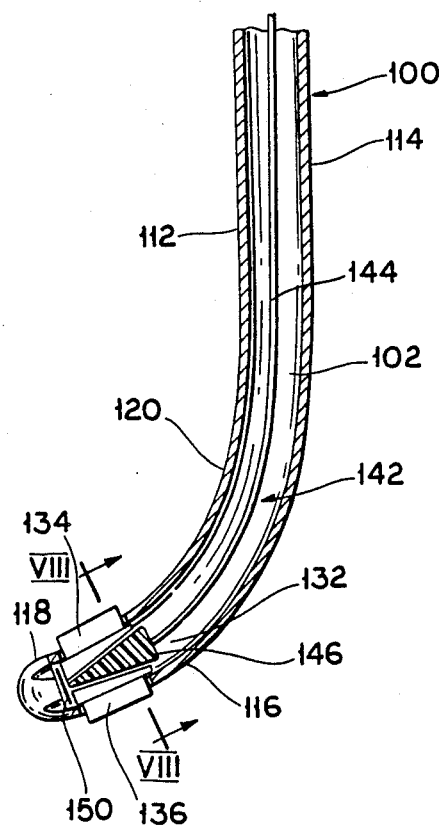
FIG. 6 is a partial cross-sectional view of a surgical tool.

Although a specific embodiment of the invention will now be described with reference to the drawings, it should be understood that the embodiment shown is by way of example only and merely illustrative of but one of the many possible specific embodiments which can represent applications of the principles of the invention. Various changes and modifications, obvious to one skilled in the art to which the invention pertains, are deemed to be within the spirit, scope and contemplation of the invention as further defined in the appended claims.

Referring to FIG. 1, a surgical suture guide 10 according to the invention consists of an elongated body 12 having a substantially straight, cylindrical portion 14. An end portion 16 with a rounded tip 18 is positioned at one end of the elongated body. A handle 26 is provided at the other end of the elongated body. A curved portion 20 is situated between the substantially straight portion and the end portion. Guide means or guide arrangement 22 with grooves 24 is located at the end portion 16 of the suture guide. The end portion 16 can be substantially straight as shown in FIG. 1 or can be a continuation of a curvature of the curved portion 20 as shown in FIG. 5.

The length of the grooves 24 can vary. They can extend from a center of the rounded tip 18 into the curved portion 20 or can be limited to the end portion 16.

FIG. 2 shows an embodiment of the invention where the guide arrangement 22 has 4 grooves which are disposed circumferentially on an outside surface of the elongated body. If desired, the guide arrangement could have one or any reasonable number of equally spaced grooves. In the cross-section the grooves can be of a triangular configuration, as shown in FIG. 2. The cross-section of the grooves can also have a triangular shaped or trapezoidal shaped configurations as illustrated in FIGS. 3 and 4.

FIG. 1 depicts that a projection of the groove 24 on the outside surface of the body defines an elongated ellipse. However, other configurations of the projection are also contemplated. For example, FIG. 5 shows the projection having a shape of a cone with a point facing the rounded tip.

During urological surgery the urethra is often divided in a substantially perpendicular fashion at the apex of the prostate to preserve as much urethral length as possible. The urethral stump retracts into the adjacent tissue such as the urogenital diaphragm. The entire prostate is removed and a new bladder neck is created. The urethrovesical anastomosis is now ready to be constructed.

Figure 12:
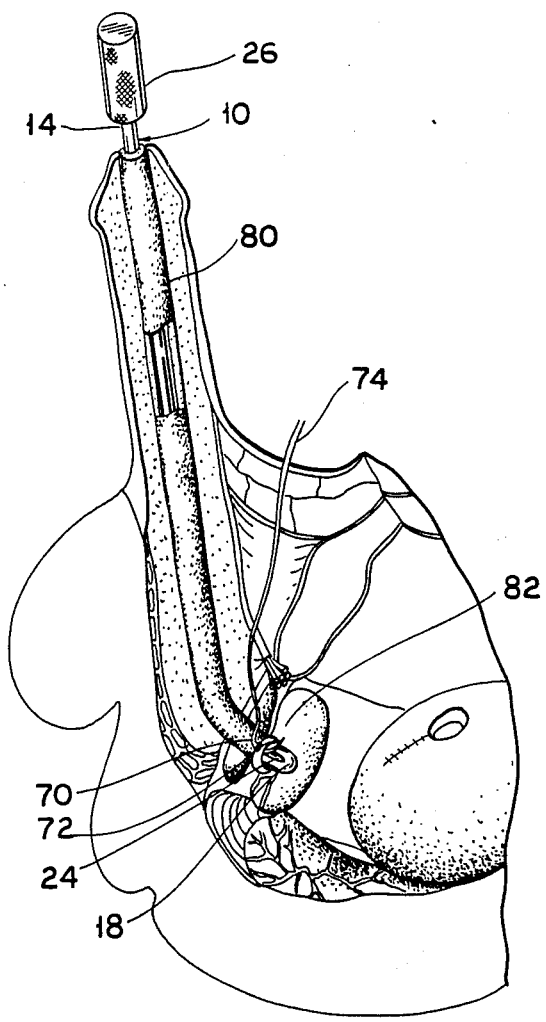
FIG. 12 illustrates use of the surgical suture guide during a urological surgery.

At this point as it shown in FIG. 12, the metal suture guide 10 is placed into and through the cut urethral meatus 80 in such a way that at least the rounded tip 18 and a part of the groove or grooves 24 of the suture guide protrude from the cut meatus pushing it out of adjacent tissue. Because the rounded tip 18 of the guide is large and blunt and the cut urethra is contracted, an in and out motion of the guide pushes the urethral stump 82 into view.

FIG. 12 illustrates that a suturing device 70 such as a needle 72 with thread 74 is inserted into the protruding groove and is supported and guided along the groove 24 while sutures are placed in the urethral meatus in the vicinity of the groove. By manipulating the handle 26 all sides of the urethral stump can be easily exposed. Rotating of the handle 26 and the substantially straight portion 14 of the guide move the grooves 24 around a circumference of an internal surface of the cut urethral meatus exposing additional sites for suture placement. Other suturing devices such as staplers, etc. are also included within this invention.

In some embodiments of the invention the sutures are placed from outside to inside direction approximately 0.5 cm to 1.0 cm from the cut edge of the urethra. However, placement of the sutures, size or type of suture will vary with the condition being treated and other factors well known to those skilled in the art. It has proved useful to use 2-0 chromic catgut suture material on needle as the suturing device. The first two sutures are usually placed at the 10-o'clock and 2-o'clock positions. The curved needle tip finds the deep grooves in the suture guide and is directed through the urethral stump. Slight traction on these sutures accompanied by in and out movement of the suture guide fully exposes the cut end of the urethra. The next two sutures can be conveniently placed at the 4-o'clock and 8-o'clock positions. Placing the suture at the 6-o'clock position is facilitated by exerting downward motion on the handle of the guide thus raising the posterior urethra, and the suture at the 12-o'clock position is placed last. However, in various circumstances other placement and order of placement may be used.

As the sutures were placed outside to inside, the same needles can be used as the suturing device for bladder anastomosis. The suture guide is now removed, and the sutures are placed through the new bladder neck. In one embodiment, a catheter is inserted into the bladder, which is then inflated with 10 mL of sterile water. The retractors are released so that the bladder can descend into the pelvis, and the sutures are tied. A useful sequence is the typing sutures at the 6-, 4-, 8-, 2-, 10-, and 12-o'clock positions. The anastomosis can now be tested for leakage by irrigation through a special catheter. If the urethra is not mobile or has been cut too short, the suture guide is helpful in providing access for the placement of sutures in an inside to outside manner. Though outside to inside sutures may also be placed.

Figure 13:
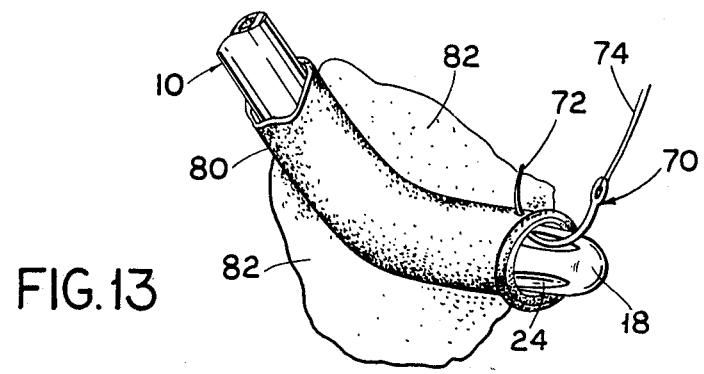
FIG. 13 illustrates use of the surgical suture guide for placement of surgical sutures through any cut portion of a body of an animal including a human having a tubular configuration.

The surgical suture guide of the invention is not limited to the urological use only. It can be used for placing surgical sutures through any cut portion of a body of an animal including a human having a tubular configuration. It is shown in FIG. 13 that during such use the suture guide 10 is inserted into and through the cut tubular part 80 of the body surrounded by an adjacent tissue 82. The guide is inserted in such a way that at least the rounded tip 18 and a part of the groove 24 are exposed from the cut tubular portion pushing it out of the adjacent tissue. The suturing device 70, 72, 74 is inserted into the protruding groove and is supported and guided by the groove 24 while sutures are placed in the tubular part.

All the sides of the tubular part are exposed by manipulating the handle of the guide (not shown in FIG. 13). To expose new sites for suture placement the handle is rotated to move the grooves around a circumference of an internal surface of the tubular part.

A cross-section of another embodiment of the invention is shown in FIG. 6. An elongated body 112 of a surgical tool 100 is made from a tubular structure having a substantially hollow inside part 102. Similar to the embodiment of FIG. 1, the embodiment of FIG. 6 contains a substantially straight portion 114, an end portion 116 and a rounded tip 118. A curved portion 120 is situated between the substantially straight portion and the end portion.

Figure 7:
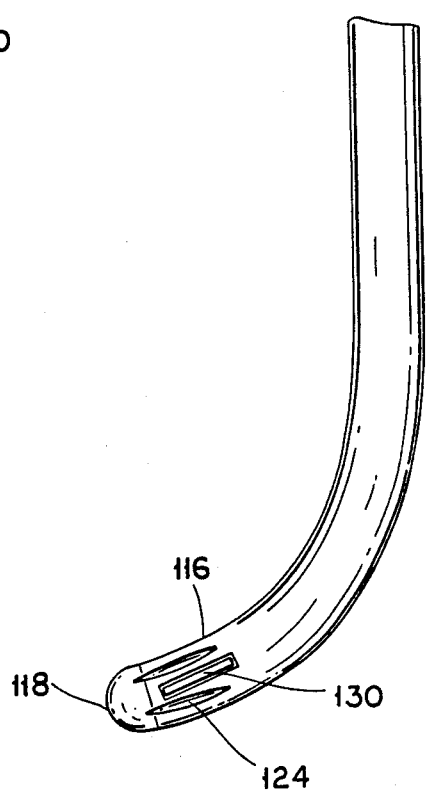
FIG. 7 is a partial general view of the elongated body shown in FIG. 6.

FIG. 7 illustrates an opening 130 going through a tubular wall of the end portion 116. The openings 130 can be limited to the end portion or can extend into the curved portion 120.

FIG. 6 shows that expanding means or arrangement 132 with at least two expanding members 134 and 136 is situated at the end portion 116 and within the hollow part 102. As it is illustrated in FIGS. 9A, 9B and 9C, each expanding member consists of a base part 138 and contacting part 140. Side walls 141 and 143 of the contacting part are guided by sides of the openings 130 when the expanding members expand during operation of the tool. A working surface 145 of the contacting part can be plain and smooth as shown in FIG. 6. However, if a different contact between the working surface 145 and an inside surface of the urethra is needed the working surface with a plurality of ribs can be used (see FIG. 9).

Figure 8:
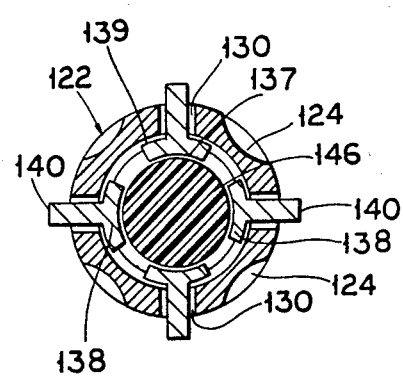
FIG. 8 is a cross-sectional view according to sectional lines VIII—VIII of FIG. 6.

A guide arrangement 122 with grooves 124 positioned between the expanding numbers 134 and 136 is situated within the wall of the end portion. FIG. 8 illustrates an embodiment of the invention with four expanding members and grooves. However, the surgical tool can have any number of equally spaced expanding members and grooves.

Generally, each base part 138, as illustrated in FIGS. 6, 8 and 9, is configured as a wedge-type member having an inside part 137 with an arc-shaped cross-section. An outside surface 139 of the base part is substantially wider than the width of the opening 130, preventing the base part from leaving the hollow area during the operation of the tool.

An activating arrangement 142 consists of an activating element 144 which is attached to an inserting element 146. The activating element 144 is made of a wire or any other type suitable flexible material. The activating element can be energized mechanically by pulling and pushing at its distal end or by any other means. FIG. 6 depicts contacting element 146 having a frustoconical configuration which is adapted to be slidably received by the inside arc-shaped surfaces 137 of the base members. However, the inside surfaces 137 of the base parts and the inserting element 146 can be of any suitable configuration adapted for mutual, slidable contact.

During the operation of the surgical tool 100, the contacting element is forced by the activating element 144 between the inside surfaces 137 of the base parts, spreading the expanding members and causing the contacting parts 140 guided by the openings 130 to expand beyond the outside surface and the elongated body.

A resilient device in a form of o-ring 150 is provided at one end of the expanding members 136 and 134 to keep them together. The o-ring 150 keeps the expanding members together during the expansion and causes the expanding members to collapse within the hollow part 102 when the contacting element 146 is withdrawn from full contact with the inside surfaces of the base parts.

The rounded tip 118 is removable to facilitate placement into and removal the expanding elements from the hollow inside part 102 of the surgical tool.

Figure 10:
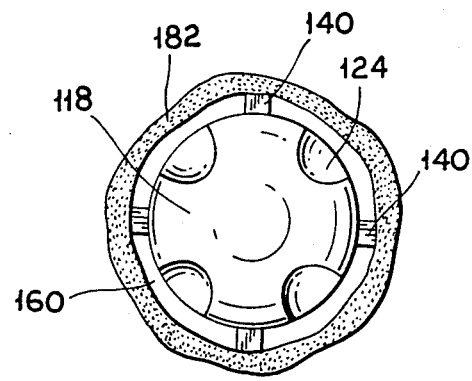
FIG. 10 is a partial front view of the surgical tool of FIG. 6 and a urethral meatus in the engaged condition.

In use the surgical tool 100 is inserted through the urethral meatus to the extent that the rounded tip 118 and a part of the grooves 124 are slightly protrude from the cut meatus (see FIG. 10).

At this time, the inserting element 146 by means of the activating element 144 is inserted between the inside surfaces 137 of the expanding members. As a result, the contacting parts 140 guided by the opening 130 are extended beyond the outside surface of the elongated body pressing against and closely contacting with the inside surface of the cut urethral meatus 182 (see FIG. 10). The improved contact reduces slippage between the tool and the meatus and substantially facilitates pushing the cut meatus out of the adjacent tissue.

When the expanding elements are in the expanded condition and the contacting parts 140 are protruded beyond the outside surface of the elongated body, a gap 160 is defined between the urethral meatus and the surgical tool (see FIG. 10) facilitating the insertion of the suturing device therebetween.

FIG. 11 illustrates a further embodiment of the invention. A surgical tool 200 has an elongated body 212 made of a tubular structure with a substantially hollow part 202 which is similar to that shown in FIG. 6. There are four openings 230 going through the tubular wall of the end portion 216. A rounded tip 218 is positioned at one end of the elongated body, the other and is semi-open.

An expanding arrangement 232 is positioned within the hollow part 202 of the elongated body. An arrangement similar to the expanding arrangement 232 has been previously described in U.S. Pat. No. [4,590,938] to Segura et al which the present application incorporates by reference.

The expanding arrangement 232 comprises four outwardly bowed spring arms or expanding members 250. At one end these spring arms are jointed at and attached to an inside surface of the rounded tip [118]. At the other end the spring arms are jointed at a place of junction between the expanding arrangement 232 and an activating element 244. During the manufacturing, each spring arm can be made of an individual element or two spring arms can be combined into a pair. It is shown in FIG. 11 that the activating element 244 of this embodiment is defined by the continuation of the spring arms. Opposed pairs of arms as well as each individual arm can be formed each of a single length of wire or stripform material or other suitable means.

In use of the surgical tool, the spring arms 250 by pulling and pushing of the activating element 244 are moved from a collapsed to an expanded condition and vice versa. In the collapsed condition the arms 250 are situated within the hollow part 202. In the expanded condition, the spring arms are guided by the openings 230 within the tubular wall and protrude through these opening beyond the outside surface of the end portion of the elongated body.

Guiding grooves 224 are positioned within the tubular wall between each two adjacent openings 230.

During the operation when the surgical tool 200 is inserted through the cut urethral meatus in such a way that at least a part of rounded tip 218 and guiding grooves 224 is extended from the cut meatus 282, the spring arms 250 are moved from the collapsed to the expanded condition. As a result, the spring arms guided by the openings 230 extend beyond the outside surface of the elongated body contacting with the inside surface of the cut urethral meatus. The tension of the tissue of the meatus produced by the spring action of the arms substantially improve the contact between the surgical tool and the cut meatus facilitates pushing the meatus out of the adjacent tissue. Similar to the embodiment of FIG. 6, during the expansion of the spring arms, a gap 260 is defined between the end portion 216 and the inside surface of the meatus. This gap substantially simplifies the insertion of the suturing device between the guide grooves 224 and the cut meatus and the placement of sutures.

The surgical tools shown in FIGS. 6–11 are not limited to a urological use only. Actually, these tools can be used for placing surgical sutures through any cut portion of a body of an animal including a human having a tubular configuration.

What is claimed is:

1. A method of placing urethral sutures through a cut portion of an urethral meatus wherein said urethral meatus is surrounded by an adjacent tissue by means of a suture guide;
    said suture guide comprising
        an elongated body having a substantially straight portion, an end portion with a rounded tip at one end of the elongated body, a curved portion situated between said substantially straight portion and said end portion, guide means having at least one groove extending from said tip into said curved portion;
    said method comprising of the following steps:
        (a) inserting said suture guide into and through the urethral meatus in such a way that at least said rounded tip and a part of said groove protrude from said cut urethral meatus pushing said cut urethral meatus out of the adjacent tissue;
        (b) inserting a suturing device into said protruding groove; and
        (c) supporting and guiding said suturing device along the groove while placing a suture in the urethral meatus.

2. A method according to claim 1 further comprising the following steps:
    (d) manipulating said substantially straight portion to expose another site of the cut urethral meatus for placing the sutures; and
    (e) repeating the steps of "b", "c" and "d".

3. A method according to claim 2 wherein the step "d" further includes rotating of said substantially straight portion and moving said groove around an internal surface of the cut urethral meatus and exposing an additional site for suture placement.

4. A method according to claim 1 wherein a handle is provided at an end of the substantially straight portion.

5. A method according to claim 1 wherein in the "b" step the suturing device is inserted between an inside surface of the urethral stump and said groove.

6. A method according to claim 1 wherein said groove has a substantially triangular cross-section.

7. A method according to claim 1 wherein said groove has an arc shaped cross-section.

8. A method according to claim 1 wherein said groove has a substantially trapezoidal-shaped cross-section.

9. A method according to claim 1 wherein a projection of said groove on an outside surface of the elongated body defines an elongated ellipse.

10. A method according to claim 1 wherein a projection of said groove on an outside surface of the elongated body defines a cone.

11. A method of placing surgical sutures through a cut portion of a body of an animal, including a human, having a tubular configuration, wherein said tubular portion is surrounded by adjacent tissue, by means of a suturing guide,
    said suturing guide comprising
        an elongated body having a substantially straight portion, an end portion with a rounded tip at one end of the elongated body, a curved portion situated between said substantially straight portion and said end portion, guide means having at least one groove extending from said tip into said curved portion;
    said method comprising of the following steps:
        (a) inserting said suture guide into and through the cut tubular part in such a way that at least said rounded tip and a part of said groove protrudes from said cut portion of the body pushing said cut portion of the body out of the adjacent tissue;
        (b) inserting a suturing device into said protruding groove; and
        (c) supporting and guiding said suturing device along the groove while placing a suture in the part of the body having tubular configuration.

12. A method according to claim 11 further comprising the following steps:
    (d) manipulating said substantially straight portion to expose another site of the tubular part for placing the sutures; and
    (e) repeating the steps of "b", "c" and "d".

13. A method according to claim 12 wherein the step "d" further includes rotating of said substantially straight portion and moving said groove around an internal surface of the tubular part and exposing an additional site for suture placement.

14. A surgical tool comprising an elongated body made of a substantially hollow tubular structure, said elongated body having a substantially straight portion, an end portion and a rounded tip at one end of the elongated body, a curved portion situated between said substantially straight portion and said end portion, at least two openings going through a wall of said substantially hollow tubular structure, said openings extending from said rounded tip to at least said end portion, guide means having at least two grooves positioned circumferentially within at least said end portion for guiding a suturing device, and
    expanding means having at least two expanding members positioned within the hollow tubular structure, each said expanding member having an engaging portion to be guided by said openings, activating means partially situated within said hollow tubular structure for activating said expanding members in such a manner that at least an engaging portion of each said expanding member passes through said opening and protrudes beyond an outside surface of the elongated body.

15. A surgical tool according to claim 14 wherein said groove is positioned within said engaging portion.

16. A surgical tool according to claim 14 wherein said grooves positioned with the substantially hollow tubular structure between said openings, said grooves extending to said rounded tip in such a manner that a substantial part of the rounded tip separates the grooves from a free end of the rounded tip.

17. A surgical tool according to claim 16 wherein each said expanding member has a base portion with upper and lower surfaces and the engaging portion is connected to the upper surface of the base portion.

18. A method of placing surgical sutures through a cut portion of a body of an animal, including a human having a tubular configuration, wherein said tubular portion is surrounded by adjacent tissue, by means of a suturing guide, said suturing guide comprising;

an elongated body made of a substantially hollow tubular structure, at least two openings going through a wall of said substantially hollow tubular structure, guide means having at least one groove for guiding a suturing device, and expanding means having at least two expanding members positioned within the hollow tubular structure, each said expanding member having an engaging portion to be guided by said openings, activating means partially situated within said hollow tubular structure for activating said expanding members in such a manner that at least the engaging portion of each said expanding member passes through said opening and protrudes beyond an outside surface of the elongated body;

said method comprising the following steps:
(a) inserting said suturing guide into and through the cut tubular portion in such a way that at least a part of said groove protrudes from said cut portion of the body, pushing said cut portion of the body out of the adjacent tissue;
(b) activating said expanding members by said activating means in such a manner that at least the engaging portion of each said expanding member passes through said opening and protrudes beyond an outside surface of the elongated body pressing against and closely contacting with an inside surface of the cut portion of the body reducing slippage between the suturing guide and the cut portion of the body and further pushing the cut portion of the body out of the adjacent tissue;
(c) inserting said suturing device into said groove; and
(d) supporting and guiding said suturing device along the groove while placing a suture in the cut portion of the body.

19. A method according to claim 18 further comprising the following steps:
(e) manipulating said elongated body of the suturing guide to expose another site of the tubular part of placing the sutures; and
(f) repeating the steps of "b", "c", and "d".

20. A method according to claim 19 wherein the step "e" further includes rotating of said elongated body of the suturing guide and moving said groove around an internal surface of the tubular part and exposing an additional site for suture placement.

21. A method according to claim 18 wherein said elongated body has an end portion and a rounded tip at one end of the elongated body, and a curved portion situated between said substantially straight portion and said end portion.

22. A method according to claim 18 wherein said groove of said guide means is positioned within the wall of the substantially hollow tubular structure between said openings, said groove extends from said rounded tip into at least said end portion.

23. A method according to claim 22 wherein said expanding members are spaced apart, outwardly bowed spring arms joined at and attached to an inside surface of said rounded tip, said spring arms are also joined at a place of juncture between said activating means and said expanding members, said spring arms are adapted to move from a first-contracting position to a second-expanding position, during said first position said spring arms are situated within the hollow tubular structure, and during said second position said activating means presses said spring arms causing them to expand and to protrude through said openings beyond the outside surface of the elongated body.

24. A method according to claim 18 wherein said groove is positioned within said engaging portion.

25. A method according to claim 24 wherein each said expanding member has a base portion with upper and lower surfaces and the engaging portion is connected to the upper surface of the base portion.

26. A method according to claim 25 wherein said activating means comprising a frusto-conical member, the lower surface of the base portion is adapted to closely receive an outside surface of the frusto-conical member, whereby, when said frusto-conical member is inserted between said engaging members, an outside surface of the frusto-conical member engages the lower surfaces of the base portion of each said expanding member pressing said engaging portions to protrude beyond the outside surface of the elongated body.

27. A surgical tool comprising an elongated body made of a substantially hollow tubular structure, said elongated body having a substantially straight portion, an end portion and a rounded tip at one end of the elongated body, a curved portion situated between said substantially straight portion and said end portion, at least two openings going through a wall of said substantially hollow tubular structure, expanding means having at least two expanding members positioned within the hollow tubular structure, each said expanding member having an engaging portion to be guided by said openings, activating means partially situated within said hollow tubular structure for activating said expanding members, said expanding member has a base portion with upper and lower surfaces and the engaging portion is connected to the upper surface of the base portion, said activating means having a frusto-conical member, the lower surface of the base portion is adapted to closely receive and outside surface of the frusto-conical member, whereby, when said frusto-conical member is inserted between said engaging members, an outside surface of the frusto-conical member engages the lower surfaces of the base portion of each said expanding members, pressing said engaging portions to protrude beyond an outside surface of the elongated body.

28. A surgical tool according to claim 27 wherein said openings extending from said rounded tip to at least said end portion, guide means having at least one groove for guiding a suturing device, and at least an engaging portion of each said expanding member passes through said opening and protrudes beyond an outside surface of the elongated body.

* * * * *